United States Patent
Crossman et al.

(10) Patent No.: US 7,972,349 B2
(45) Date of Patent: Jul. 5, 2011

(54) BLOOD SAMPLING DEVICES

(75) Inventors: David Danvers Crossman, Oxford (GB); Jeremy Marshall, Oxford (GB)

(73) Assignee: Owen Mumford Limited, Oxford (GB)

(*) Notice: Subject to any disclaimer, the term of this patent is extended or adjusted under 35 U.S.C. 154(b) by 303 days.

(21) Appl. No.: 10/520,507

(22) PCT Filed: Aug. 2, 2004

(86) PCT No.: PCT/GB2004/003314
§ 371 (c)(1),
(2), (4) Date: Oct. 4, 2005

(87) PCT Pub. No.: WO2005/013825
PCT Pub. Date: Feb. 12, 2005

(65) Prior Publication Data
US 2006/0129172 A1 Jun. 15, 2006

(30) Foreign Application Priority Data
Aug. 6, 2003 (GB) .................................. 0318366.2

(51) Int. Cl.
*A61B 17/14* (2006.01)
*A61B 17/32* (2006.01)
(52) U.S. Cl. .................. 606/182; 600/583; 606/181
(58) Field of Classification Search .......... 606/181–183; 215/231, 318; 600/583
See application file for complete search history.

(56) References Cited

U.S. PATENT DOCUMENTS

| 3,165,220 | A | * | 1/1965 | Haynes | 215/318 |
|---|---|---|---|---|---|
| 4,817,603 | A | * | 4/1989 | Turner et al. | 606/182 |
| 5,324,303 | A | | 6/1994 | Strong et al. | |
| 5,487,748 | A | * | 1/1996 | Marshall et al. | 606/181 |
| 5,628,765 | A | * | 5/1997 | Morita | 606/182 |
| 5,741,288 | A | | 4/1998 | Rife | |
| 5,755,733 | A | | 5/1998 | Morita | |
| 2004/0243165 | A1 | * | 12/2004 | Koike et al. | 606/181 |

FOREIGN PATENT DOCUMENTS

EP  0 255 338  2/1988
(Continued)

OTHER PUBLICATIONS

JP Office Action dated Apr. 22, 2010 from corresponding JP Application No. 2006-522396.

*Primary Examiner* — Max Hindenburg
*Assistant Examiner* — John Pani
(74) *Attorney, Agent, or Firm* — Young & Thompson

(57) ABSTRACT

A housing retains a lancet body which encloses a needle whose tip is covered by a cap. The cap has a head provided with flanges. These flanges locate within notches at the end of the housing on only two sides of the housing. The location of the flanges within the notches holds the lancet within the body, before use, so as to compress a spring positioned between a head and a slotted portion of the housing. When the device is to be used, the head of the cap is rotated through 90° so as to detach the cap from the rest of the lancet body and release the flanges from the notches. This allows the lancet body to be actuated by a sprung-loaded trigger-release mechanism, when required, so that the tip of the needle projects momentarily through the opening at the end of the housing and then bounces back.

6 Claims, 2 Drawing Sheets

FOREIGN PATENT DOCUMENTS

| | | |
|---|---|---|
| JP | 07-016218 | 1/1995 |
| JP | 11-349015 | 12/1999 |
| JP | 11-349016 | 12/1999 |
| JP | 2000-109104 | 4/2000 |
| WO | 96/16599 | 6/1996 |
| WO | WO 02/43591 | 6/2002 |
| WO | WO 03005907 A1 * | 1/2003 |

* cited by examiner

BLOOD SAMPLING DEVICES

BACKGROUND TO THE INVENTION

1. Field of the Invention

A blood sampling device includes a needle-carrying lancet, a housing and a cap.

2. Description of the Related Art

A conventional form of blood sampling device comprises a lancet which is sprung-loaded within a housing so that, upon release of a trigger, the lancet is driven forward to cause a needle tip to project momentarily from an end of the housing to prick the skin of a patient in order to enable a blood sample to be taken. For transportation before use, the needle is covered by a removable cap and the lancet is held within the housing in the sprung loaded condition. There is, however, always the possibility of inadvertent release of the trigger. It is an object of this invention to provide a blood sampling device of this nature which provides greater security against release of the lancet from the housing during transportation before use.

SUMMARY OF THE INVENTION

Accordingly, there is provided a blood sampling device comprising a needle-carrying lancet located within a housing and having a cap positioned over the needle, the cap extending to project through an opening at one end of the housing and having one or more locating members fitting into one or more cooperating features of the outer walls of the housing, the cap being twistable to release the locating members from the cooperating features such that the cap can be detached from the housing and from the needle.

Ideally the or each locating member is a flange or rib and the or each cooperating feature is a groove, or vice versa. There could be two flanges fitting into grooves in two opposed sides of the outer walls of the housing.

The cap holds the lancet securely within the housing during transportation, even if pressure is inadvertently applied to the trigger which would otherwise release a drive mechanism to cause a spring to drive the lancet out of the housing. Before use, the user will rotate the cap relative to the rest of the lancet to enable the cap to be detached and removed from the tip of the needle. This rotation will also release the locating members from the cooperating features, thus enabling the cap to be detached from the device whilst leaving the lancet in its primed state.

In the invention, the trigger releasable latch and said lancet have respective opposed latch surfaces cooperable to retain the lancet in the housing until release of the latch, and the cap is adapted to hold the lancet in a position in which the lancet latch surface is spaced rearwardly of the latch surface of the trigger-releasable latch until said cap is detached from the housing and from the lancet.

In the preferred arrangement, the lancet is sprung loaded to urge the lancet in the direction towards the opening in the housing.

Ideally the device will include a trigger-releasable latch to hold the lancet within the housing such that an exposed needle cannot project through said opening until the latch is released by the trigger.

BRIEF DESCRIPTION OF THE DRAWING FIGURES

The invention may be performed in various ways and a preferred example thereof will now be described, with reference to the accompanying diagrammatic drawings, in which.

DETAILED DESCRIPTION OF THE INVENTION

Figure 1:
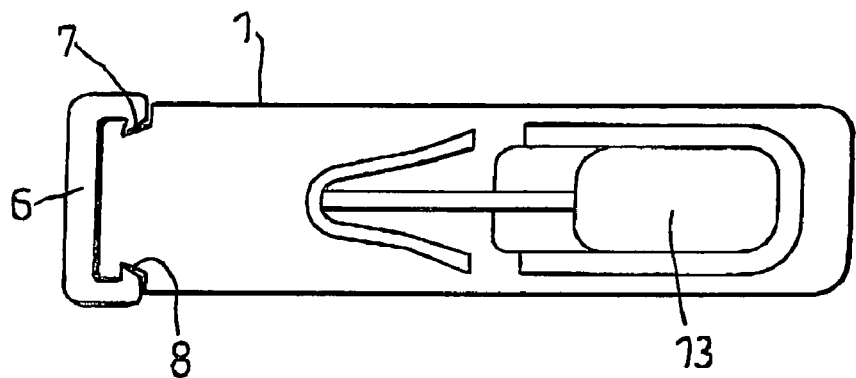
FIGS. 1 and 2 are plan and side views respectively of a blood sampling device of this invention.
Figure 2:
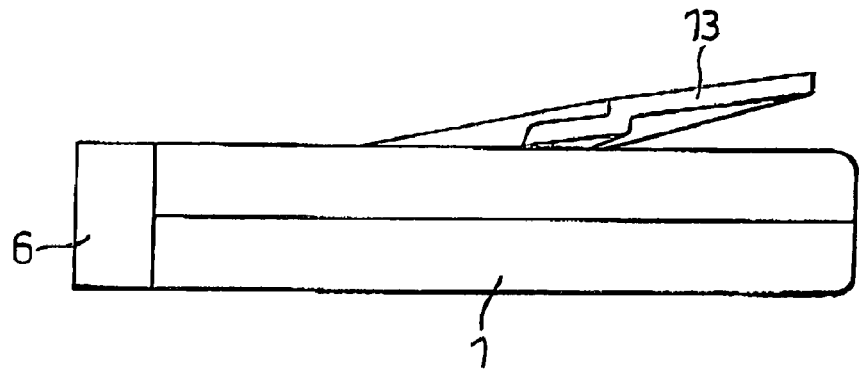
Figure 3:
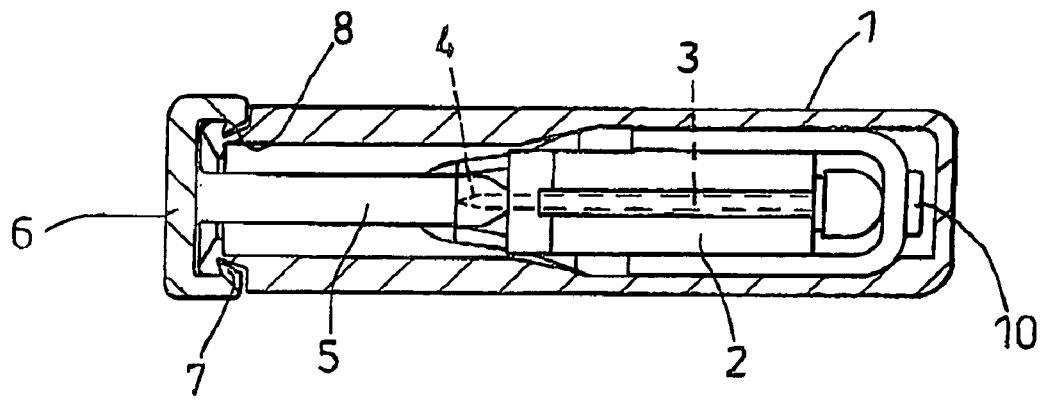
FIG. 3 is a partial cross-section through the device of FIGS. 1 and 2.
Figure 4:
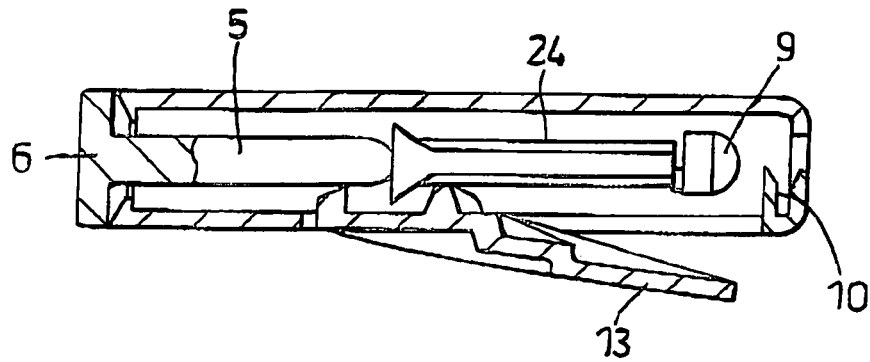
FIGS. 4 to 6 show, in cross-section, the device of FIGS. 1 and 2 in varying stages of use.

The device shown in FIGS. 1 to 3 comprise a housing 1 retaining a lancet body 2. As can be seen particularly from FIG. 3, the lancet body encloses a needle 3 whose tip 4 is covered by a cap 5. The other end of the cap has a head 6 provided with flanges 7. These flanges locate within notches 8 at the end of the housing 1. As can be seen from FIG. 4, the flanges 7 and notches 8 are provided only on two sides of the housing 1.

Figure 5:
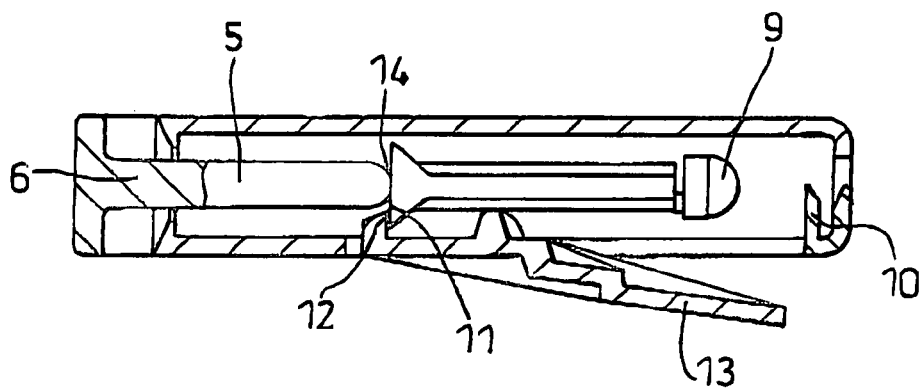
Figure 6:
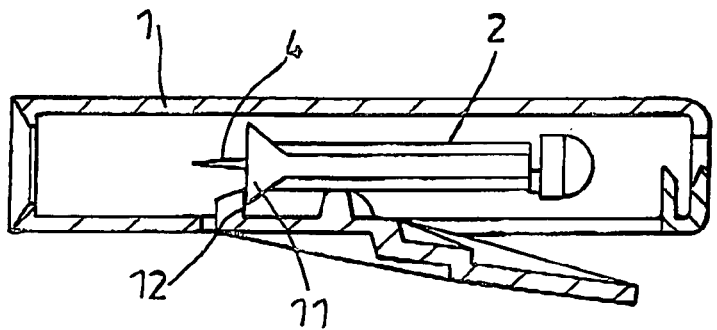

The location of the flanges 7 within the notches 8 holds the lancet 2 within the body 1 so as to compress a spring (not shown) positioned between a head 9 and a slotted portion 10 of the housing 1. When the device is to be used, the head 6 of the cap 5 is rotated through 90° so as to release the flanges 7 from the notches 8 in the two sides of the housing 1. This allows the lancet body 2 to move forwards (under the bias of the spring) until a ledge 11 on the lancet locates against a flange 12 on the trigger member 13 (FIG. 5). Twisting of the cap 5 also releases the cap from the rest of the lancet body 2 at a weakened area 14. The cap can then be removed to expose the tip 4 of the needle within the housing 1, as shown in FIG. 6. The blood sampling device can now be actuated by pressing the trigger 13 so that the flange 12 is released from the ledge 11. This causes the lancet to be driven forwards by the spring so that the tip 4 of the needle projects momentarily through the opening at the end of the housing 1 and then bounces back.

The invention claimed is:

1. A blood sampling device comprising:
    a housing;
    a spring loaded needle-carrying lancet located within the housing;
    a cap releasably attached to said lancet adjacent said needle; and
    a trigger-releasable latch to hold the lancet within the housing such that an exposed needle cannot project through an opening at one end of the housing until the latch is released by the trigger,
    the cap extending to project from an attachment to said lancet through the opening at one end of the housing and having at least one locating member fitting into at least one cooperating feature of an outer wall of the housing, and the cap holding the lancet against movement relative to the housing, the cap being twistable to release the at least one locating member from the at least one cooperating feature such that the cap can be detached from the housing and from the lancet, the lancet having a spring loading to urge the lancet in a direction towards the opening in the housing,
    wherein said trigger releasable latch and said lancet have respective opposed latch surfaces engageable to retain said lancet in said housing until release of said latch, and said cap is adapted to hold the lancet in a position in which the lancet latch surface is spaced rearwardly of and out of engagement with the latch surface of said trigger-releasable latch until said cap is detached from the housing and from the lancet.

2. The blood sampling device according to claim 1, wherein the at least one locating member and the at least one cooperating feature are fitted together via a groove cooperating with a flange or a rib.

3. The blood sampling device according to claim 2, wherein there are two flanges fitting into grooves in two opposed sides of the outer walls of the housing.

4. The blood sampling device according to claim 1, wherein a head of the cap can be rotated 90° to release flanges from notches in two sides of the housing.

5. The blood sampling device according to claim 4, wherein the lancet can move forward until a ledge on the lancet locates against a flange on the trigger.

6. The blood sampling device according to claim 1, wherein the cap holds the lancet against at least forward movement relative to the housing.

* * * * *